United States Patent [19]
Hassfeld et al.

[11] Patent Number: 5,807,252
[45] Date of Patent: Sep. 15, 1998

[54] METHOD AND APPARATUS FOR DETERMINING THE POSITION OF A BODY PART

[75] Inventors: Stefan Hassfeld, Dossenheim; Joachim Mühling, Buchen; Theodor Lutze, Balgheim; Joachim Schulz, Tuttlingen, all of Germany

[73] Assignee: Aesculap AG, Germany

[21] Appl. No.: 735,032

[22] Filed: Oct. 22, 1996

[30] Foreign Application Priority Data

Feb. 23, 1995 [DE] Germany ............... 195 06 197.7

[51] Int. Cl.⁶ .................................................. A61B 19/00
[52] U.S. Cl. ..................... 600/407; 606/130; 378/206; 128/897
[58] Field of Search ........................ 128/653.1, 898, 128/664, 665; 606/130, 59, 65, 73, 104; 356/247; 378/205, 206; 600/407, 473, 476

[56] References Cited

U.S. PATENT DOCUMENTS

| | | |
|---|---|---|
| 4,471,786 | 9/1984 | Inagaki et al. . |
| 4,826,487 | 5/1989 | Winter . |
| 5,127,407 | 7/1992 | Tan . |
| 5,178,164 | 1/1993 | Allen . |
| 5,230,623 | 7/1993 | Guthrie et al. . |
| 5,315,630 | 5/1994 | Sturm et al. . |
| 5,325,862 | 7/1994 | Lewis et al. . |
| 5,383,454 | 1/1995 | Bucholz . |
| 5,389,101 | 2/1995 | Heilbrun et al. . |
| 5,392,779 | 2/1995 | Meredith et al. . |
| 5,662,111 | 9/1997 | Cosman . |
| 5,697,929 | 12/1997 | Mellinger . |
| 5,707,373 | 1/1998 | Sevrain et al. . |
| 5,728,136 | 3/1998 | Thal . |

FOREIGN PATENT DOCUMENTS

| | | |
|---|---|---|
| 0 413 588 A2 | 2/1991 | European Pat. Off. . |
| 0 429 148 A1 | 5/1991 | European Pat. Off. . |
| 38 38 011 | 7/1989 | Germany . |
| 39 37 555 | 5/1991 | Germany . |
| WO 94/17733 | 8/1994 | WIPO . |

OTHER PUBLICATIONS

"Halbleiter–Positionsdetektoren," *Markt & Technik*, Nr. 34, Aug. 26, 1983, pp. 28 and 31.

Primary Examiner—Marvin M. Lateef
Assistant Examiner—Shawna J. Shaw
Attorney, Agent, or Firm—Barry R. Lipsitz

[57] ABSTRACT

To improve the reliability of a process for determining the position of a body part in which bone screws are screwed into the bone of the body part in question, each bone screw is provided with a radiation emitter or radiation receiver. A number of fixed receivers or emitters are used as appropriate to receive radiation from the bone screw transmitters or direct radiation towards the bone screw receivers. The radiation direction and/or radiation propagation time and/or radiation field strength or frequency is used to determine the position of each radiation emitter or receiver. A system for determining position based on this procedure and bone screws which can be used therefor are also disclosed.

16 Claims, 2 Drawing Sheets

5,807,252

METHOD AND APPARATUS FOR DETERMINING THE POSITION OF A BODY PART

This application is a continuation of International PCT Application No. PCT/EP95/04954, filed on Dec. 14, 1995.

BACKGROUND OF THE INVENTION

The invention relates to a method for determining the position of a body part, wherein bone screws are screwed into the bone of the body part. The invention further relates to a system for determining the position of a body part comprising several radiation emitters or radiation receivers, respectively, and several stationary receivers or emitters, respectively, and also a data processing device which determines the positions of the radiation emitters or radiation receivers, respectively, from the direction and/or the propagation time of the transmitted radiation.

Finally, the invention also relates to a bone screw.

In medical operations, in particular, in head operations, it is standard practice to compile exact data on the internal body structures, for example, by means of a computer-assisted tomogram, before the operation and to then make these available during the operation, for example, in the form of sectional pictures of the brain on a monitor. To enable exact spatial coordination, marking elements, so-called fiducials, are immovably fixed on a body part during the pre-operative examinations. These are, for example, bone screws which are screwed into the skull and protrude slightly over the scalp. When the layer pictures are taken, for example, by means of computer-assisted tomograms or nuclear spin tomograms, these marking elements are visible and, therefore, for example, the relative position of a sectional plane which has been taken can be checked in relation to the examined head by means of these marking elements.

During the operation itself, these marking elements remain in the body. After the body part has been moved to a desired position at the beginning of the operation, the layer pictures taken can be made to coincide (correlated) with the pertinent body part on the basis of these marking elements.

During the operation, however, movements of the body part cannot be excluded, and the coordination of the momentary position of the body part with the pertinent layer picture, for example, with treatment apparatus, is then no longer correct.

It is, therefore, attempted to fix and clamp the body in holding frames. However, this is not always possible as the body part often has to be moved during the operation.

Systems which measure such movement of the body part and determine the momentary position of the body part are known. These operate with radiation emitters or radiation receivers which in the known systems are attached to holding frames which, in turn, are fixed on the body part. Such holding frames, for example, so-called Mayfield clamps, are normally cumbersome devices which can also be used for holding instruments. In practice, it has been found that the fixing of radiation receivers or radiation emitters on such clamps or frames does enable determination of the position of the frame or the clamp and hence determination of the position of the body part held in the frame, but that the accuracy of such determination leaves much to be desired. In such arrangements, the radiation emitters and radiation receivers are located at a relatively large distance from the body part, and, furthermore, slight displacements between the body part and the frame cannot be excluded with the necessary certainty, and, therefore, the positioning of the emitters and receivers on the body part can change slightly in the course of an operation.

The object of the invention is to so configure a generic method that increased reliability of the determining of the momentary position of the monitored body part is possible.

SUMMARY OF THE INVENTION

This object is accomplished in accordance with the invention in a method of the kind described at the outset in that a radiation emitter or a radiation receiver is arranged on the bone screw, and in that with several stationary receivers or emitters, respectively, radiation is received from the radiation emitters or radiation is directed towards the radiation receivers, respectively, and the position of each radiation emitter or radiation receiver, respectively, is determined from the radiation direction and/or the radiation propagation time and/or the strength or frequency of the radiation fields.

Accordingly, the essence of the invention is that the radiation receivers or radiation emitters are no longer fixed on a frame or a clamp at a relatively large distance from the body part to be monitored, but directly on the bone screws which are screwed into the body part and are, therefore, immovable with the necessary certainty relative to the body part. It is thereby ensured that the radiation emitters or radiation receivers, respectively, reliably maintain their relative position in relation to the monitored body part throughout the entire operation. In all, a considerably increased accuracy of the position monitoring is thus achieved. In addition, this method can also be used when use of a frame or a clamp attached to the body part is dispensed with in certain operations. The bone screws screwed into the body part in any case can be used for fixing the radiation receivers or radiation emitters, respectively, and serve as marking elements for the correlation of body part and layer pictures. It is expedient for a light emitting diode to be used as radiation emitter. This emits radiation which can be received by stationary radiation receivers. Of course, a radiation receiver for visible radiation could also be arranged on the bone screws, but it is advantageous to fix the radiation emitter on the bone screw as the radiation emitters are normally smaller than the radiation receivers.

Other physical emitter/receiver combinations are also conceivable, for example, ultrasonic transmitters and ultrasonic receivers or radiation emitters and radiation receivers in the invisible range, points reflecting light and radiation receivers or coils which receive and transmit electromagnetic radiation.

It is expedient to use bone screws which only protrude a few millimeters over the surface of the body part. Hence there are no large lever arms between body part and radiation emitter or radiation receiver, respectively, i.e., the relative position of the radiation emitter or the radiation receiver, respectively, in relation to the body part is, in this case, practically unchanged.

Normally, quite a large number of bone screws with radiation emitter or with radiation receiver, respectively, will be used in order to thereby determine various degrees of freedom of the body part movement. It is expedient to monitor the relative position of these bone screws in relation to one another and not to take into account the positional data of a radiation emitter or radiation receiver, respectively, whose position has changed relative to the position of the remaining radiation emitters or radiation receivers, respectively, in the determining of the position of the body part. When, in the case of quite a large number of radiation emitters or radiation receivers fixed on the body part, one of these radiation emitters or radiation receivers, respectively, indicates a changed position in relation to all of the others, this is an indication that this radiation emitter or radiation receiver, respectively, has unintentionally become displaced, whether it be that it has become released from the bone screw or that the bone carrying the bone screw has itself become damaged during the operation. Once this occurs, the data processing system can independently eliminate the data of this changed radiation emitter or radiation receiver, respectively, and determine the position of the body part only on the basis of the positional data of the remaining radiation emitters or radiation receivers, respectively, and so this unintentional deviation is not included in the results of the position determination. Also, if required, a warning signal can be given to call attention to the displacement of a radiation emitter or a radiation receiver, respectively.

In a system for determining position of the kind described at the outset, the aforementioned object is accomplished in accordance with the invention in that the radiation emitters or radiation receivers are arranged on bone screws.

It is expedient for the radiation emitters or radiation receivers to be inserted in the bone screw, for example, in a screw-in opening in the bone screw which can accommodate a screw-in tool when the radiation emitters or radiation receivers, respectively, have been removed.

The invention also relates to a bone screw which is characterized in that it carries a radiation emitter or a radiation receiver.

The following description of a preferred embodiment of the invention serves in conjunction with the drawings to explain the invention in further detail.

DETAILED DESCRIPTION OF THE INVENTION

Figure 2:
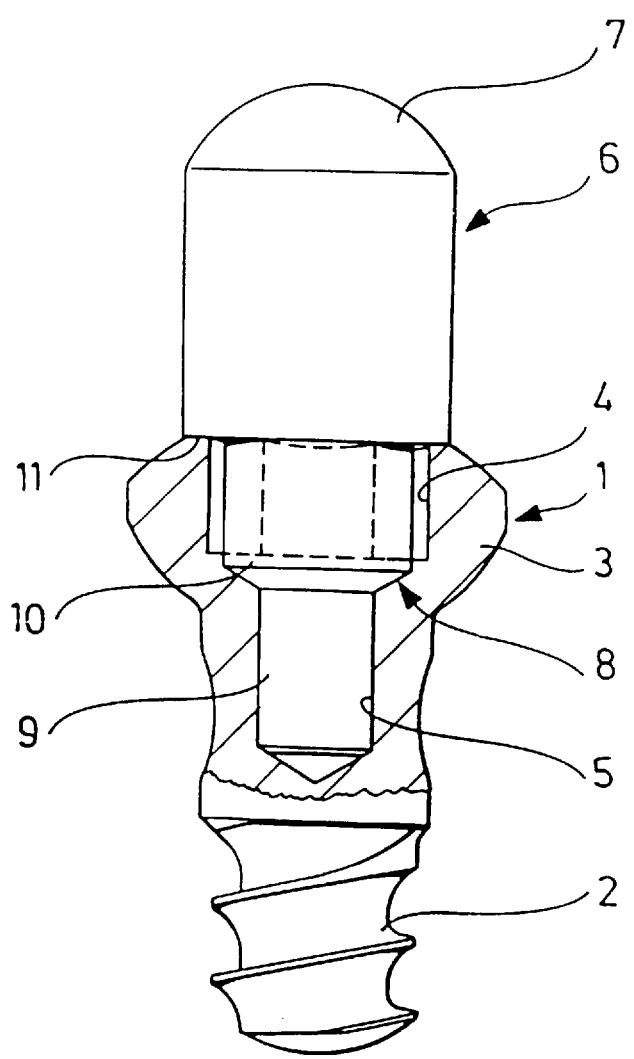
FIG. 2: a part-sectional view of a bone screw with an inserted light emitting diode as radiation emitter.

FIG. 2 shows a conventional bone screw 1 with a thread 2, a head 3 and a hexagonal insert opening 4 arranged in the head for a screw-in tool. Adjoining the insert opening 4, at the bottom thereof, concentrically with the insert opening 4, is a cylindrical blind hole bore 5.

Inserted into this bone screw 1 is a light emitting diode 6 comprising a diode head 7 and an insert foot 8. With an insert pin 9, the insert foot engages the blind hole bore 5 and is held with a press fit therein. A widening 10 of the insert foot 8 is received in the insert opening 4 of the bone screw 1.

With its underside 11, the diode head 7 is supported on the upper edge of the head 3 and, in the inserted state, thus assumes a precisely defined position with respect to the bone screw 1. In a manner not apparent from FIG. 2, the light emitting diode 6 is connected via a cable to an energy source so that, as required, the light emitting diode 6 can be made to emit light. Such a cable 12 is apparent from the illustration in FIG. 1.

Figure 1:
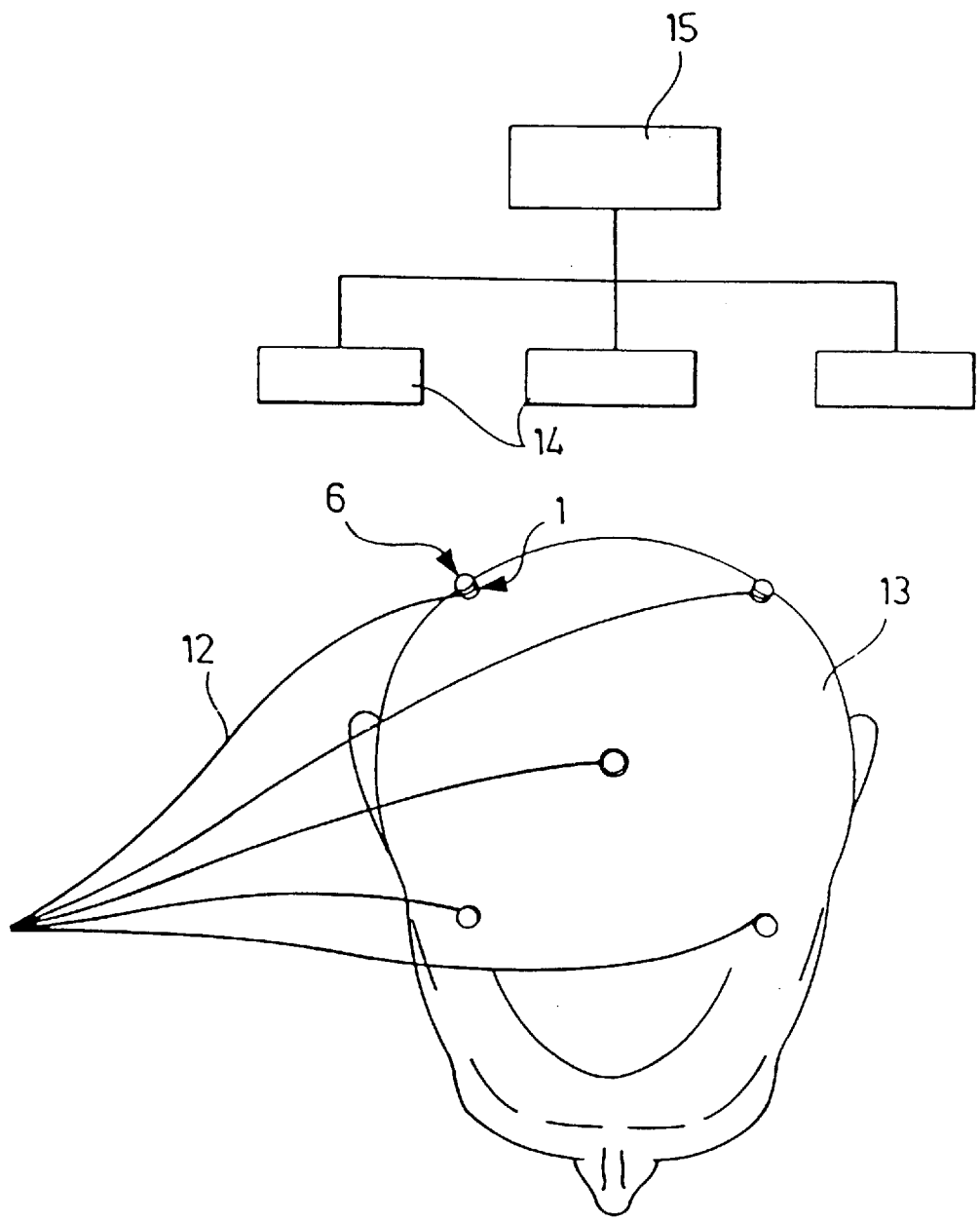
FIG. 1: a schematic view of a system for determining position.

FIG. 1 also shows how several bone screws 1 can be fixed in any chosen pattern on a body part, in the illustrated example, on the head 13 of a patient. In a pre-operative examination, the bone screws 1 are screwed in this desired pattern into the skull bone of the patient where they form in the surrounding area of the planned operation site a pattern of marking elements or fiducials which are also detected by computer-assisted tomograms and, therefore, when sectional pictures are taken, their position relative to the head 13 of the patient can be determined.

During a subsequent operation, light emitting diodes 6 are inserted into each bone screw 1 and then connected via cables 12 to a common energy and control source. The radiation emitted by the light emitting diodes 6 impinges on several stationary radiation receivers 14, and, in particular, owing to their different arrangement, with a different incidence angle, and, possibly, also after a different propagation time. These data are fed by the radiation receivers 14 to a data processing system 15 which on the basis of these different data determines the relative position of each light emitting diode 6 in relation to the radiation receivers 14. Determining the position of all light emitting diodes 6 results in a complete determination of the position and orientation of the head 13. This determination of position and orientation can be continuously repeated throughout the entire operation and, therefore, also upon movement of the head 13 relative to the radiation receivers 14, the relative position can be determined at any time.

If the position of a light emitting diode 6 relative to the position of the other light emitting diodes should change, this will also be detected by the data processing system, and this is then an indication that, unexpectedly, either the corresponding light emitting diode 6 is no longer held correctly in the associated bone screw 1 or even this bone screw itself is no longer fixed in the intended manner on the head 13. In such a case, the positional data of this bone screw 1 and this light emitting diode 6 are ignored by the data processing system 15 and not used in determining the position and orientation of the head, and, therefore, erroneous determinations cannot occur. In addition, where appropriate, a warning signal can be generated to point out to the operator that this erroneously positioned light emitting diode has to be checked.

The light emitting diodes 6 can be removed from the bone screws 1 simply by pulling them out, and so the patient can be provided with remaining bone screws 1 after the operation. These bone screws 1 can, for example, prove to be of importance in a subsequent examination, for example, when taking new sectional pictures.

What is claimed is:

1. An apparatus for determining the position of a body part, comprising:
   (a) a unitary bone screw having a threaded end and an opposing driven end;
      said threaded end being adapted to threadedly engage the body part to affix said bone screw thereto;
      said bone screw comprising a bore hole which extends from said driven end and through an interior portion of said bone strew toward said threaded end; and
   (b) a radiation device having an insert foot; wherein:
      said bore hole is sized to receive and engage said insert foot to secure said radiation device therein in a defined position with respect to said bone screw; and
      said radiation device comprises one of a radiation emitter and a radiation receiver.

2. The apparatus of claim 1, wherein:
   said insert foot is secured in said bore hole via a press fit.

3. The apparatus of claim 1, wherein:
   said driven end comprises a polygonal insert opening which is adapted to receive a corresponding polygonal tool for driving said bone screw.

4. The apparatus of claim 1, wherein:

the radiation device is removeably receivable in said bore hole.

5. The apparatus of claim 1, wherein:

said bone screw is adapted to be used alone as a marking element.

6. The apparatus of claim 1, wherein:

said bone screw is sized to protrude only a few millimeters over a surface of the body part when affixed thereto.

7. The apparatus of claim 1, wherein:

said body part comprises a skull bone.

8. The apparatus of claim 1, wherein:

said radiation device comprises a light-emitting diode with a diode head;

an underside of said diode head is supported on an upper edge of said driven end when said insert foot is secured in said bore hole.

9. A system for determining the position of a body part comprising a plurality of the bone screws and respective radiation devices of claim 1, comprising:

a plurality of stationary receivers or emitters for communicating with the respective radiation devices;

a data processing device which determines the positions of the radiation devices based on characteristics of radiation which is communicated between the radiation devices and the stationary receivers or emitters;

said characteristics including at least one of direction, propagation time, strength and frequency of the radiation.

10. The system of claim 9, wherein:

at least three of said bone screws are used to determine the position of the body part;

said data processing device monitors the relative position of the radiation devices with respect to one another; and in determining the position of the body part, said data processing device ignores the positional data of one of said radiation devices whose position has changed with respect to the position of the remaining radiation devices.

11. A method for determining the position of a body part, wherein bone screws are screwed into the bone of the body part, comprising the steps of:

providing a unitary bone screw with a bore hole extending from a head portion thereof toward a threaded portion thereof;

providing a radiation device with an insert foot;

inserting said insert foot into said bore hole to removably secure said insert foot therein;

arranging a plurality of stationary receivers or emitters for communicating with the radiation devices of the respective bone screws; and determining the positions of the radiation devices based on characteristics of radiation which is communicated between the radiation devices and the stationary receivers or emitters;

said characteristics including at least one of direction, propagation time, strength and frequency of the radiation.

12. The method of claim 11, wherein:

said radiation device comprises a light-emitting diode.

13. The method of claim 11, wherein:

said bone screws are sized to protrude only a few millimeters over a surface of the body part when affixed thereto.

14. The method of claim 11, wherein at least three of said bone screws are used to determine the position of the body part, comprising the further steps of:

monitoring the relative position of the radiation devices with respect to one another; and ignoring the positional data of one of said radiation devices whose position has changed with respect to the position of the remaining radiation devices when determining the position of the body part.

15. The method of claim 11, comprising the further step of:

removing the respective radiation device from at least one of the bone screws and using the at least one bone screw alone as a marking element.

16. The method of claim 11, wherein:

said body part comprises a skull bone.

* * * * *